(12) United States Patent
Goetz et al.

(10) Patent No.: US 8,838,242 B2
(45) Date of Patent: Sep. 16, 2014

(54) PRE-CONFIGURATION OF ELECTRODE MEASUREMENT OF AN IMPLANTABLE MEDICAL DEVICE, SYSTEM AND METHOD THEREFORE

(75) Inventors: Steven M. Goetz, Brooklyn Center, MN (US); Warren W. Ball, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1087 days.

(21) Appl. No.: 12/112,523

(22) Filed: Apr. 30, 2008

(65) Prior Publication Data

US 2009/0276009 A1 Nov. 5, 2009

(51) Int. Cl.
*A61N 1/00* (2006.01)
*A61N 1/36* (2006.01)
*A61N 1/372* (2006.01)
*A61N 1/37* (2006.01)
*A61N 1/08* (2006.01)

(52) U.S. Cl.
CPC ........ *A61N 1/37247* (2013.01); *A61N 1/36185* (2013.01); *A61N 1/3706* (2013.01); *A61N 2001/083* (2013.01)
USPC .......................................................... 607/28

(58) Field of Classification Search
CPC ........... A61N 1/36153; A61N 1/36185; A61N 1/37247; A61N 1/3706; A61N 1/36157; A61N 1/36171; A61N 1/3686
USPC ..................... 607/2, 7–8, 28, 48, 62; 600/547
See application file for complete search history.

(56) References Cited

U.S. PATENT DOCUMENTS 4,870,341 A 9/1989 Pihl et al.
5,487,755 A 1/1996 Snell et al.
(Continued)

FOREIGN PATENT DOCUMENTS

WO WO 9819738 A1 5/1998
WO WO 0143821 A1 6/2001
(Continued)

OTHER PUBLICATIONS

International Search Report for PCT/US2009/030970.
(Continued)

*Primary Examiner* — Christopher D Koharski
*Assistant Examiner* — Roland Dinga
(74) *Attorney, Agent, or Firm* — IPLM Group, P.A.

(57) ABSTRACT

Method, controller and system for an implantable medical device having a plurality of electrodes, the implantable medical device capable of delivering therapeutic stimulation to a patient, comprising a control module, a user interface operatively coupled to the control module, the user interface providing control of the control module by a medical professional or other user, and an electrode interface operatively coupled between the plurality of electrodes and the control module. The control module uses the electrode interface to obtain a plurality of measurements of integrity metrics for a plurality of selected pairs of individual ones of the plurality of electrodes. The control module determines a prescriptive analysis using the plurality of measurements of integrity metrics of the selected pairs of individual ones of the plurality of electrodes comparative to a range, and the user interface displays the prescriptive analysis.

36 Claims, 7 Drawing Sheets

(56) References Cited

U.S. PATENT DOCUMENTS

| | | |
|---|---|---|
| 5,549,654 A | 8/1996 | Powell |
| 5,713,937 A | 2/1998 | Nappholz et al. |
| 5,724,985 A | 3/1998 | Snell et al. |
| 5,891,179 A | 4/1999 | Er et al. |
| 6,101,415 A | 8/2000 | Er et al. |
| 6,308,100 B1 | 10/2001 | Er et al. |
| 6,374,139 B1 | 4/2002 | Er et al. |
| 6,721,600 B2 | 4/2004 | Jorgenson et al. |
| 6,748,274 B2 | 6/2004 | Levine et al. |
| 6,842,644 B2 | 1/2005 | Anderson et al. |
| 2002/0077669 A1 | 6/2002 | Lindh et al. |
| 2002/0120307 A1 | 8/2002 | Jorgenson et al. |
| 2003/0088289 A1 | 5/2003 | Levine et al. |
| 2003/0114899 A1 | 6/2003 | Woods et al. |
| 2003/0176807 A1* | 9/2003 | Goetz et al. ............ 600/547 |
| 2003/0176899 A1 | 9/2003 | Samuelsson et al. |
| 2004/0082980 A1 | 4/2004 | Mouine et al. |
| 2004/0098063 A1 | 5/2004 | Goetz |
| 2004/0143303 A1* | 7/2004 | Sieracki et al. ............ 607/48 |
| 2004/0225337 A1 | 11/2004 | Housworth et al. |
| 2005/0010258 A1 | 1/2005 | Peterson et al. |
| 2005/0033385 A1 | 2/2005 | Peterson et al. |
| 2005/0107841 A1 | 5/2005 | Meadows et al. |
| 2006/0036186 A1* | 2/2006 | Goetz et al. ............ 600/547 |
| 2006/0259079 A1* | 11/2006 | King ............ 607/2 |
| 2006/0265025 A1 | 11/2006 | Goetz et al. |
| 2008/0103552 A1* | 5/2008 | Goetz et al. ............ 607/59 |

FOREIGN PATENT DOCUMENTS

| | | |
|---|---|---|
| WO | WO 03077992 A1 | 9/2003 |
| WO | WO 2005068017 A1 | 7/2005 |
| WO | WO 2006017277 A2 | 2/2006 |
| WO | WO 2007/102945 A2 | 9/2007 |
| WO | WO 2007/112061 A2 | 10/2007 |
| WO | WO 2007112061 A2 | 10/2007 |
| WO | WO 2007112061 A3 | 10/2007 |
| WO | WO 2008/005142 A1 | 1/2008 |
| WO | WO 2008/027885 A1 | 3/2008 |
| WO | WO 2008/054438 A1 | 5/2008 |

OTHER PUBLICATIONS

European Office Action for EP 09739267.4 dated Sep. 13, 2013.

* cited by examiner

PRE-CONFIGURATION OF ELECTRODE MEASUREMENT OF AN IMPLANTABLE MEDICAL DEVICE, SYSTEM AND METHOD THEREFORE

FIELD

The present invention relates generally to controllers, systems and methods for implantable medical devices and, more particularly, to such controllers, systems and methods for implantable medical devices having therapeutic electrodes.

BACKGROUND

The medical device industry produces a wide variety of electronic devices for treating patient medical conditions. Depending upon medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices designed to deliver therapeutic electrical stimulation include neurological stimulators, pacemakers and defibrillators.

Implantable medical devices configured to deliver therapeutic electrical stimulation commonly deliver therapy via electrodes positioned on one or more leads operatively connected to the implantable medical device. In some instances, the housing of the implantable medical device may also serve as an electrode or an electrode may be positioned on the housing of the implantable medical device. The electrode or electrodes are commonly positioned in the patient's body during the same surgical procedure in which the implantable medical device is implanted. Sometimes the electrode or electrodes are placed in a follow-up procedure.

The medical device industry produces a wide variety of electronic devices for treating patient medical conditions. Depending upon the medical condition, medical devices can be surgically implanted or connected externally to the patient receiving treatment. Medical professionals or other clinicians use medical devices alone or in combination with drug therapies and surgery to treat patient medical conditions. For some medical conditions, medical devices provide the best and sometimes the only therapy to restore an individual to a more healthful condition and a fuller life. Examples of implantable medical devices designed to deliver therapeutic electrical stimulation include neurological stimulators, pacemakers and defibrillators.

Implantable medical devices configured to deliver therapeutic electrical stimulation commonly deliver therapy via electrodes positioned on one or more leads operatively connected to the implantable medical device. In some instances, the housing of the implantable medical device may also serve as an electrode or an electrode may be positioned on the housing. The electrode or electrodes are commonly positioned in the patient's body during the same surgical procedure in which the implantable medical device is implanted.

The positioning of electrodes, and associated leads, is often an inexact procedure and may commonly be dependent on the particular physiologic characteristics of the patient.

In addition, electrodes may commonly be positioned within the patient without the medical professional or user conducting the procedure being capable of actually seeing where the electrodes are positioned. Instead, external aides such as fluoroscopes and/or endoscopes may commonly be employed to inform the medical professional or other user as to an approximate location of the electrodes during implantation. Electrodes may also be placed by stereotactic head frame which allows placement of the lead without direct visualization. Further, the ideal target is often not known a priori and time constraints may not allow for perfect targeting in the operating room.

Due to the inherent uncertainty involved in the placement of electrodes for an implantable medical device, implantable medical devices and the external controllers that interface with the devices are commonly operable to perform a test on the leads and electrodes to verify that the leads and electrodes are functioning properly and are positioned correctly. A common test is to check the impedance between pairs of electrodes. During testing, an electrode can be driven with a signal having known electrical characteristics. The signal may be measured, e.g., on another electrode or electrodes, and the impedance computed between electrodes using known fundamental relationships. The measured impedance value can give a medical professional or other user information relating to whether the electrodes involved in the test are positioned correctly and operating properly.

An external controller, or physician programmer, is commonly utilized in lead impedance tests. Physician programmers can be similar in size and composition to a large laptop computer. The physician programmer provides a user interface via a display screen, and is manipulated by a medical professional via a variety of inputs, such as buttons and touchscreens. The physician programmer commonly communicates with the implantable medical device via inductive telemetry. In order to accomplish this, a coil, operatively coupled to the controller, is placed in proximity of a coil operatively coupled to the electronics in the implantable medical device, thereby establishing an inductive link over which data may be passed in either direction. Because physician programmers are typically not sterilized, the physician programmer itself may be placed outside of the sterile field, and only the coil and its housing is taken inside the sterile field, e.g., using a sterile bag.

For example, U. S. patent application Publication No. 2006/0036186, Goetz et al, Automatic Impedance Measurement of an Implantable Medical Device; U.S. Pat. No. 5,891,179, Er et al, Method and Apparatus for Monitoring and Displaying Lead Impedance in Real-Time for an Implantable Medical Device; U.S. patent application Publication No. 2003/0114899, Samuelsson et al, Programming System for Medical Devices; U.S. patent application Publication No. 2005/0033385, Peterson et al, Implantable Medical Device Programming Apparatus Having a Graphical User Interface; and U.S. Pat. No. 6,721,600, Jorgenson et al, Implantable Lead Functional Status Monitor and Method, all disclose devices that measure electrode impedance or otherwise test electrodes of an implantable medical device.

SUMMARY

As the number of electrodes associated with an implantable medical device has increased from one or two, to just a few and then to many electrodes, the time and hardware and software resources necessary to perform proper measurements for all of the electrodes associated with an implantable medical device has, in many cases, become burdensome.

In an embodiment, a controller or system containing such a controller or a method therefore, can be pre-configured by a user to test only a subset of the total number of electrodes and electrode pair combinations available in an implantable medical device.

None of the above documents show, disclose or suggest allowing a medical professional to pre-configure electrode functionality tests in order to improve efficiency of the test by testing only such leads and electrodes as the medical professional considers necessary. The controller may provide a range of integrity metrics, e.g., impedance values, considered normal, bounded on either end by values fixed for the test. In addition, a medical professional may specify which electrodes are to be tested, and the range of integrity metrics considered normal for those particular electrodes. Inter-electrode impedance tests may also be conducted at voltage and current levels that are used by the device to deliver therapy in order to determine functionality at operation voltage levels.

In an embodiment, the present invention provides a controller for an implantable medical device having a plurality of electrodes, the implantable medical device being capable of delivering therapeutic stimulation to a patient via the plurality of electrodes. A control module is operatively coupled to the plurality of electrodes. A user interface is operatively coupled to the control module, the user interface providing at least partial control of the control module by a user. The control module obtains a plurality of measurements of integrity metrics for a group of individual ones of the plurality of the electrodes, the group of individual ones of the plurality of electrodes being based upon a selection made via the user interface.

In an embodiment, the control module obtains a plurality of measurements of integrity metrics of the individual ones of the plurality of electrodes included in a selected group of individual ones of the plurality of the electrodes selected via the user interface.

In an embodiment, the control module obtains a plurality of measurements of integrity metrics of the individual ones of the plurality of electrodes not included in a selected group of individual ones of the plurality of the electrodes selected via the user interface.

In an embodiment, the control module uses a plurality of parameters selected via the user interface to obtain the plurality of measurements of integrity metrics.

In an embodiment, the plurality of parameters are selected from the group consisting of voltage, amplitude, pulse width, frequency, current, power and electrode polarity.

In an embodiment, the user interface presents for possible measurement of impedance value only ones of the plurality of electrodes having previously received a measurement of impedance value comparative to a predetermined range.

In an embodiment, the user interface presents for possible measurement of impedance value only ones of the plurality of electrodes currently in use by the implantable medical device.

In an embodiment, the user interface presents for possible measurement of impedance value only ones of said plurality of electrodes that have previously been selected by the user.

In an embodiment, the user interface presents for possible measurement of impedance value only ones of the plurality of electrodes having previously received a measurement of impedance value comparative to a predetermined range.

In an embodiment, the user interface presents for possible measurement of impedance value only ones of said plurality of electrodes that are associated as being at least one of free of side effects or free of side effects above a predetermined threshold.

In an embodiment, the present invention provides a controller for an implantable medical device having a plurality of electrodes. The implantable medical device being capable of delivering therapeutic stimulation to a patient via the plurality of electrodes. A control module is operatively coupled to the plurality of electrodes. A user interface is operatively coupled to the control module. The user interface provides at least partial control of the control module by a user. The control module obtains a plurality of measurements of integrity metrics for one of a plurality of groups of individual ones of plurality of electrodes with the one of a plurality of groups being based upon a selection made via the user interface.

In an embodiment, at least one of the plurality of groups are determined, at least in part, on a modality of measurement.

In an embodiment, the modality of measurement is at least one of current based impedance measurement, voltage based impedance measurement, real impedance, complex impedance, number of measurement pulses, timing of measurement pulses, sampling of measurement data and oversampling of measurement data.

In an embodiment, the present invention provides a system for delivering therapeutic stimulation to a patient. The system includes an implantable medical device having a plurality of electrodes, and a controller. The controller includes a control module operatively coupled to the plurality of electrodes, and a user interface operatively coupled to the control module, the user interface providing control of the control module by a user. The control module obtains a plurality of measurements of integrity metrics for a group of individual ones of the plurality of the electrodes, the group of individual ones of the plurality of electrodes being based upon a selection made via the user interface.

In an embodiment, the present invention provides a system for delivering therapeutic stimulation to a patient. The system includes an implantable medical device having a plurality of electrodes, and a controller. The controller includes a control module operatively coupled to the plurality of electrodes, and a user interface operatively coupled to the control module, the user interface providing control of the control module by a user. The control module obtains a plurality of measurements of integrity metrics for one of a plurality of groups of individual ones of plurality of electrodes with the one of a plurality of groups being based upon a selection made via the user interface.

In an embodiment, the present invention provides a method for delivering therapeutic stimulation to a patient using an implantable medical device having a plurality of electrodes, comprising the steps of creating a selected group of individual ones of the plurality of electrodes via a user interface, and obtaining a plurality of measurements of integrity metrics for a group of individual ones of the plurality of the electrodes, the group of individual ones of the plurality of electrodes being based upon a selection made via the user interface.

In an embodiment, the obtaining step utilizes individual ones of the plurality of electrodes included in a selected group of individual ones of the plurality of the electrodes selected via the user interface.

In an embodiment, the obtaining step utilizes individual ones of the plurality of electrodes not included in a selected group of individual ones of the plurality of the electrodes selected via the user interface.

In an embodiment, the obtaining step uses a plurality of parameters selected via the user interface.

In an embodiment, the plurality of parameters are selected from the group consisting of voltage, amplitude, pulse width, frequency, current, power and electrode polarity.

In an embodiment, there is a further comprising the step of presenting via the user interface for possible measurement of impedance value only ones of the plurality of electrodes having previously received a measurement of impedance value comparative to a predetermined range.

In an embodiment, the presenting step presents for possible measurement of impedance value only ones of the plurality of electrodes currently in use by the implantable medical device.

In an embodiment, the presenting step presents for possible measurement of impedance value only ones of the plurality of electrodes having previously received a measurement of impedance value comparative to a predetermined range.

In an embodiment, the present invention provides a method for delivering therapeutic stimulation to a patient using an implantable medical device having a plurality of electrodes, comprising the steps of creating a plurality of groups of individual ones of said plurality of electrodes, and obtaining a plurality of measurements of integrity metrics for one of a plurality of groups of individual ones of the plurality of electrodes, the one of a plurality of groups being based upon a selection made via a user interface.

DRAWINGS

DESCRIPTION

While electrode tests are illustrated and described herein generally as being electrode impedance tests, it is to be recognized and understood that other forms of electrode integrity testing is also contemplated. In general, an integrity metric, which may be an impedance measurement, may be measured for a plurality of electrodes and the efficacy of each of the plurality of electrodes determined, at least in part. While electrode impedance is one such integrity metric, others are contemplated such as admittance, real or complex. Other integrity metrics could be the current flowing into or out of a particular electrode or group of electrodes, voltage potential measured at an electrode due to stimulus on another electrode or electrodes, capacitance of an electrode with respect to another electrode or electrodes, inductance of an electrode with respect to another electrode or electrodes, frequency response of an electrode with respect to stimulus on another electrode or electrodes, measured reflection of a stimulus signal driven into an electrode (as in an electromagnetic transmission line).

Figure 1:
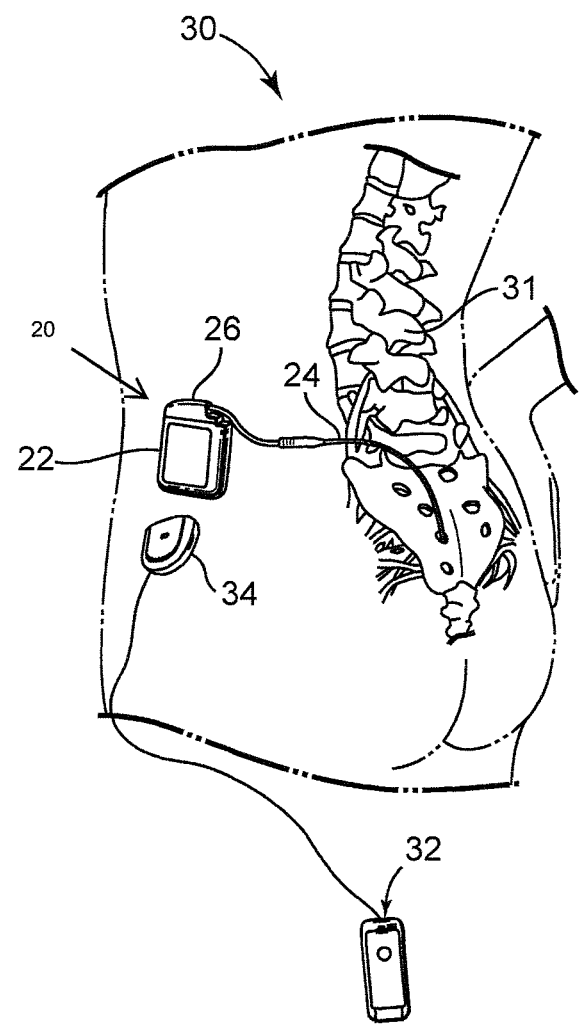
FIG. 1 shows an example of an implantable neurological stimulator implanted in the side of a patient, with electrodes positioned along the patient's sacral nerves.

FIG. 1 shows the general environment of one rechargeable implantable medical device 20 embodiment. Implantable neurological stimulator 22 is shown, but other embodiments such as pacemakers and defibrillators and the like are also applicable. Implantable neurological stimulator 22 is implanted subcutaneously in side 28 of patient 30. Lead 24 is operatively coupled to implantable neurological stimulator 22 at header 26. Lead 24 is positioned along spinal chord 31 of patient 30. Controller 32, which may be a physician programmer or patient programmer, may become transcutaneously coupled to implantable neurological stimulator 22 via an inductive communication link through the tissue of patient 30 when controller 32 is placed in proximity to implantable neurological stimulator 22.

Figure 2:
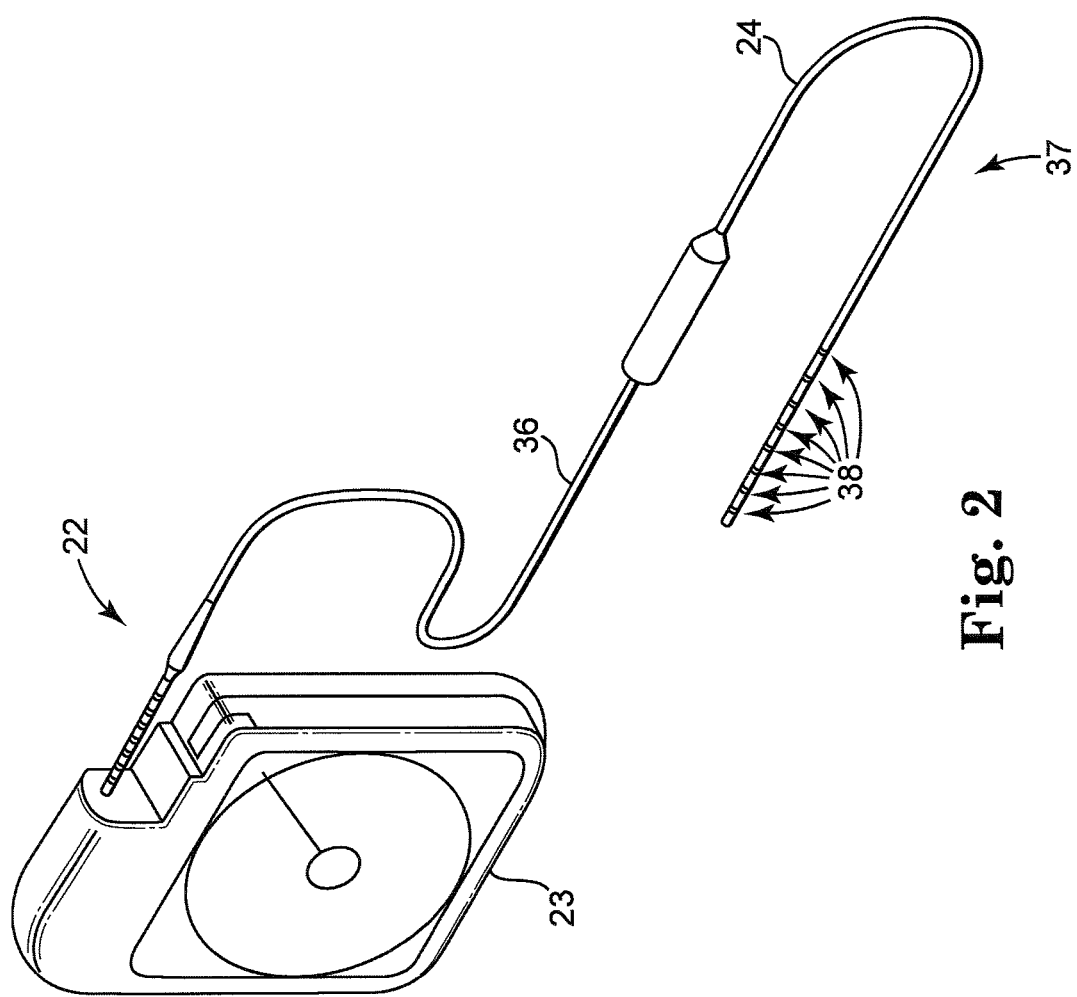
FIG. 2 shows an implantable neurological stimulator with a lead and lead extender and electrodes.
Figure 3:
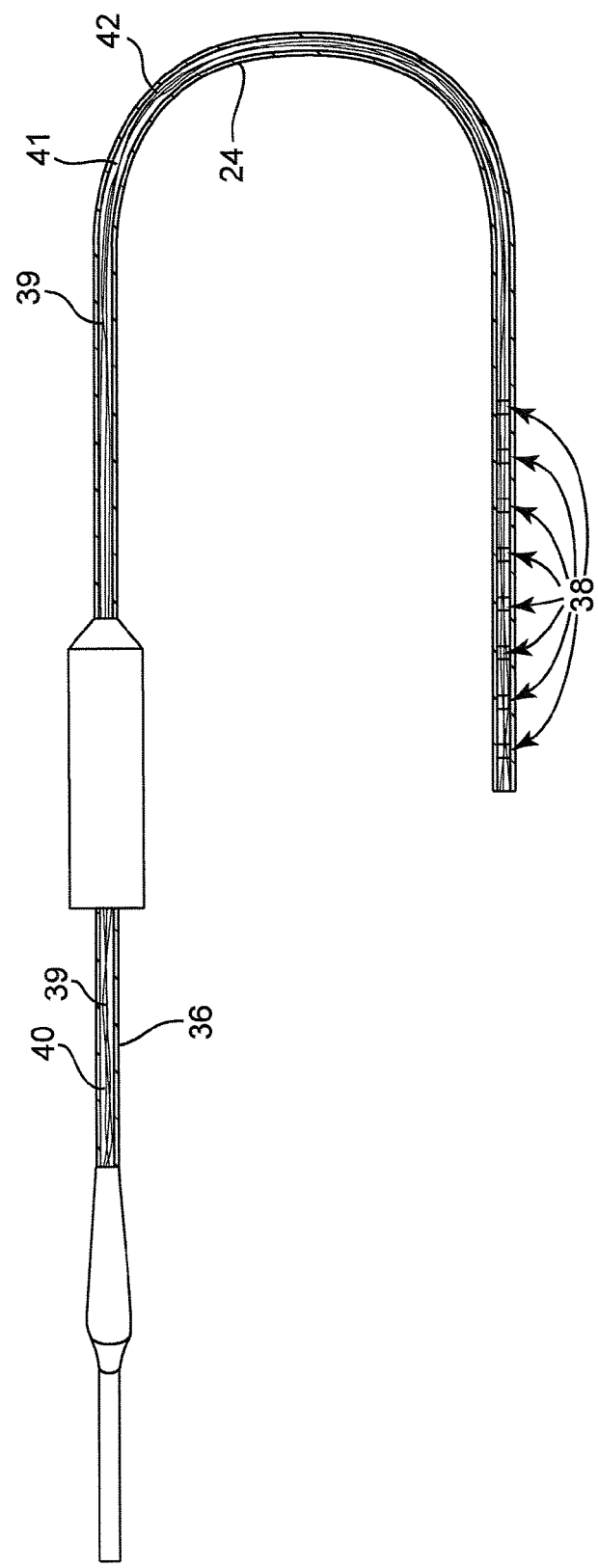
FIG. 3 shows a cutaway diagram of a lead with electrodes, and a lead extender, for an implantable medical device.

FIGS. 2 and 3 show a closer view of implantable neurological stimulator 22 and lead 24, operatively coupled by extender 36. Electrodes 38 are mounted on distal end 37 of lead 24. Electrodes 38 are comprised of a conductive material, in an embodiment, metal, that come into direct contact with tissue of patient 30. Electrodes 38 are operatively coupled with implantable neurological stimulator 22 via header 26 through wires 39 comprised of conductive material that pass through the interior 41 of lead 24 and are operatively coupled with conductive wires 39 in the interior 40 of extender 36.

Figure 4:
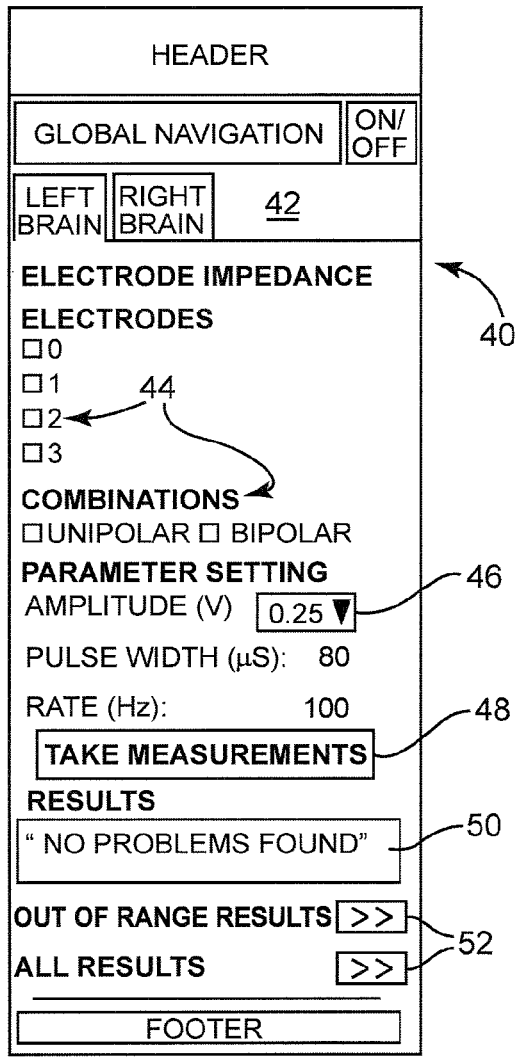
FIG. 4 shows a screen shot of a window for controlling an electrode impedance test of an implantable neurological stimulator.

FIG. 4 shows electrode impedance panel 140 for neurological stimulator 22, in this case a deep brain stimulator. Pick menus 142 allow selection of different leads 24 to test. Pick boxes 44 allow the medical professional or other user to select which electrodes 38 will be tested and whether those electrodes 38 will be tested in unipolar or bipolar configuration. Scroll menu 46 allows the medical professional or other user to set the voltage amplitude, and optionally, pulse width and frequency, at which point the test will be conducted. Pressing button 48 begins the test according to the parameters that have been chosen on panel 140. Alternatively, the test may begin without the necessity of a button press. After the test has completed a summary of the results is displayed in window 50, while buttons 52 give the medical professional or other user access to panel 60 (FIG. 5) that displays all results that were out of the predetermined range and to panel 80 (FIG. 6) that displays all results.

In a typical electrode impedance test, each electrode 38 will be tested both in unipolar mode and bipolar mode. Each electrode 38 in unipolar mode is paired up with neurological stimulator case 23 and the impedance between each electrode 38 and implantable neurological stimulator case 23 is measured and stored. In addition, each electrode 38 in bipolar mode is paired up with every other electrode 38 and the impedance between each electrode 38 and every other electrode 38 is measured and stored. An exception may be that electrodes 38 that are located in different physiologic regions of the body, e.g., the head, the chest, are never paired and tested.

Figure 5:
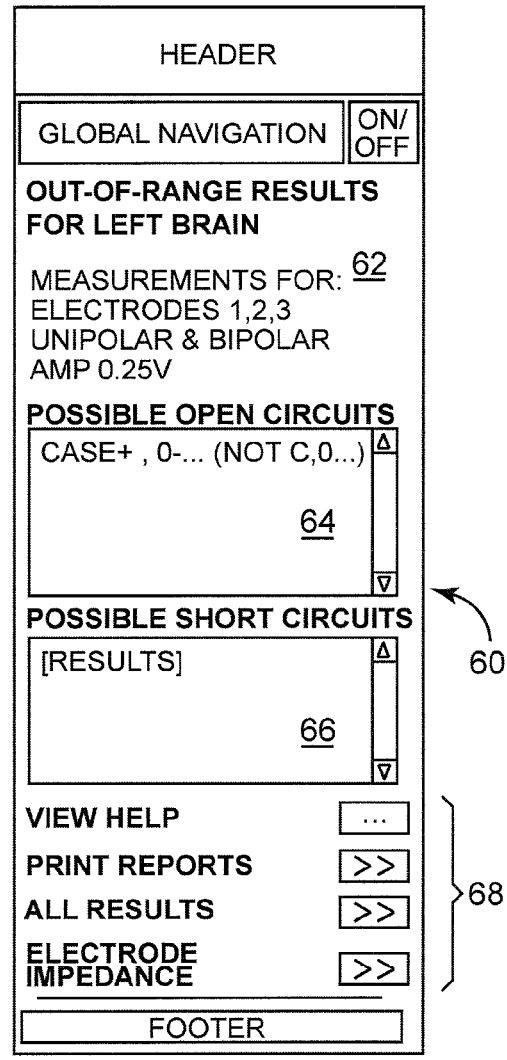
FIG. 5 shows a screen shot of a window for displaying out-of-range results of an electrode impedance test of an implantable neurological stimulator.

FIG. 5 shows out of range results panel 60 for displaying the results of testing initiated from electrode impedance panel 140. Text 62 at top of out of range results panel 60 informs the medical professional or other user what test the current results pertain to by displaying which electrodes 38 were tested, in which mode electrodes 38 were tested and at which voltage amplitude electrodes 38 were tested. Possible open circuits window 64 lists possible locations, e.g., all possible locations, of open circuits that cause faults of tested electrodes 38. Possible short circuits window 66 lists possible locations, e.g., all possible locations, of short circuits that cause faults.

Open circuits are typically detectable when all measured impedance values for one electrode 38 are higher than the allowable maximum value. For instance, if all impedance values involving electrode (38) number two exceed the maximum value and all impedance values not involving electrode 38 number two are within the allowable value, the controller could conclude that an open circuit existed on the path along which electrode (38) number two was operatively coupled with implantable neurological stimulator 22. Similarly, if all measured impedance values pertaining to electrodes (38) number two and six exceeded the maximum value and all impedance values not involving electrodes (38) number two and six are within the allowable a values, the controller could conclude that both electrodes (38) number two and six were open.

By contrast, short circuits are typically detectable when all measured impedance values involving those two electrodes (38) are lower than average and the measured impedance value between the two electrodes 38 is below the minimum allowable value. For instance, if the average impedance between electrodes (38) is five hundred ohms, but between electrodes (38) four and five, and four and six, in bipolar mode, and electrodes (38) five and case 23 and six and case 23 were all four hundred ohms, and the impedance between electrodes 38 five and six was below the allowable minimum value, controller 120 (FIG. 7) could conclude that there is a short circuit between electrodes (38) five and six. Such short circuits can occur, among other reasons, because the electrodes 38 in question are physically touching, or insulation 42 between wires 39 operatively coupling electrodes 38 with implantable neurological stimulator 22 have frayed. Other examples of possible electrodes shorts are crushing of the lead body causing conductive wires to contact each other or adjoining wires and fluid ingress to a connector, e.g., lead to lead extension, lead extension to implantable medical device, lead to implantable medical device, causing one or more of the electrodes to short.

Occasionally, the results of testing may provide ambiguous results. For instance, if the impedance between electrodes (38) zero and two, three and two and between electrode (38) two and case 23 are all greater than the maximum allowable value, but the impedance between electrodes (38) one and two is within the allowable range, then it might not be clear what is the underlying cause of the issue.

Figure 6:
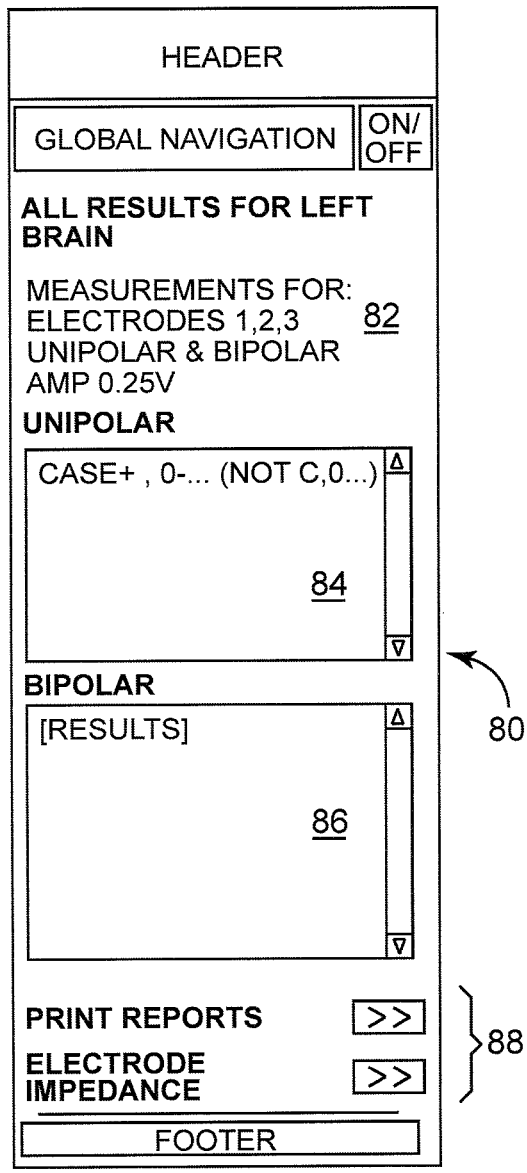
FIG. 6 shows a screen shot of a window for displaying results of an electrode impedance test of an implantable neurological stimulator.

FIG. 6 shows all results panel 80, for displaying all results of testing initiated from electrode impedance panel 140, regardless of whether testing resulted in an indication of failure or failures or not. Text 82 at the top of all results panel 80 informs the medical professional or other user to what test the current results pertain by displaying which electrodes 38 were tested, in which mode electrodes 38 were tested and at which voltage amplitude electrodes 38 were tested. Results are displayed in one of two windows 84, 86 depending on if the test mode was unipolar 84 or bipolar 86. Buttons 88 provide access to electrode impedance panel 140 and a print command.

Figure 7:
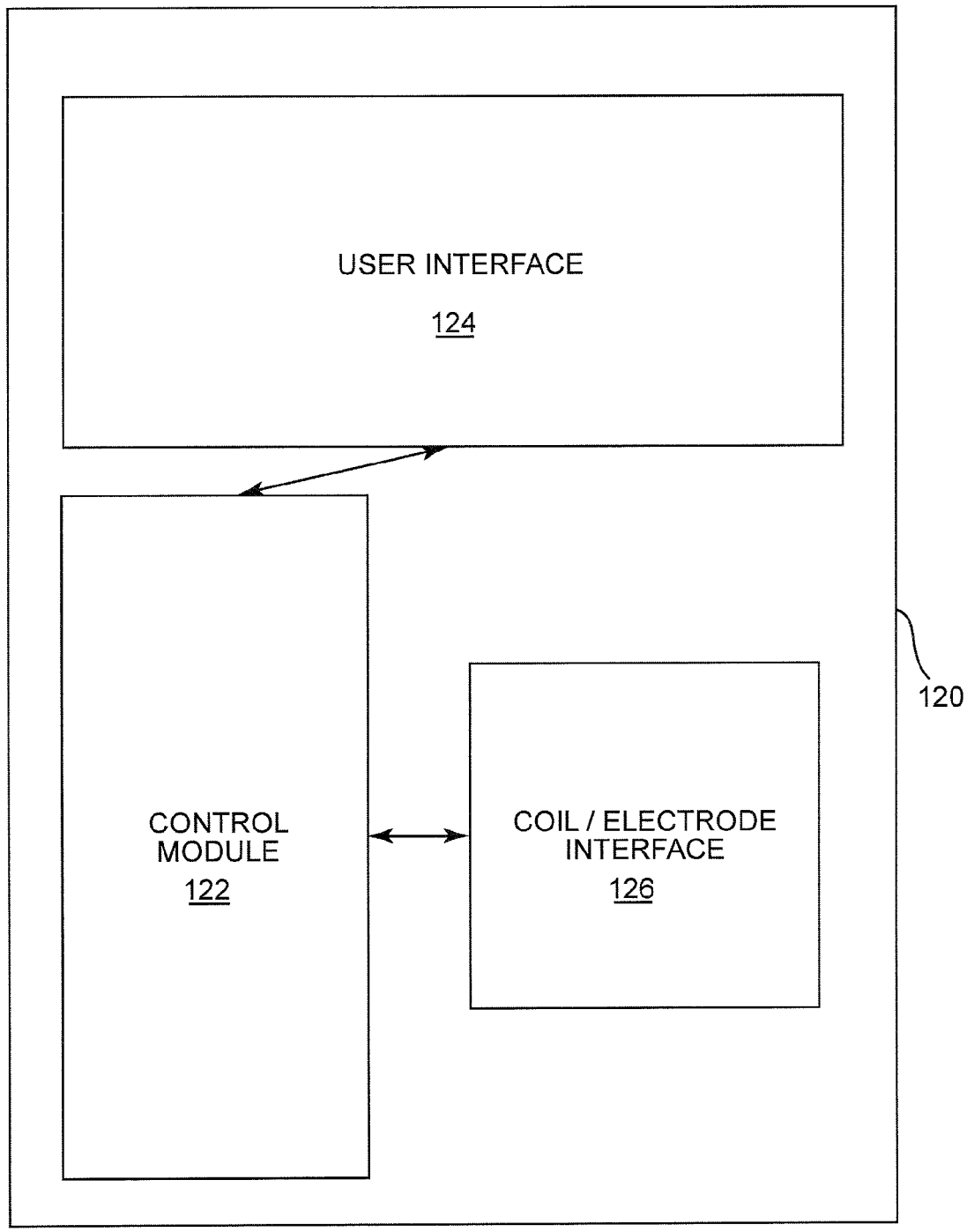
FIG. 7 shows a block diagram of a controller for an implantable medical device.

FIG. 7 shows a block diagram of the functional blocks of controller 120, which may be employed as, and be similar to, controller 32 of FIG. 1. Control module 122 comprises a variety of off the shelf electronic components commonly found in a variety of commercial applications, such as personal computers. These electronic components include: a microprocessor, RAM, ROM and hard disks. These off the shelf components are integrated into control module 122 and additional operational features are added via custom electronics. These custom electronics are comprised of off the shelf integrated circuits and discrete components, and programmable components, such as FPGAs and DSPs, and custom integrated circuits and PCBs.

Figure 8:
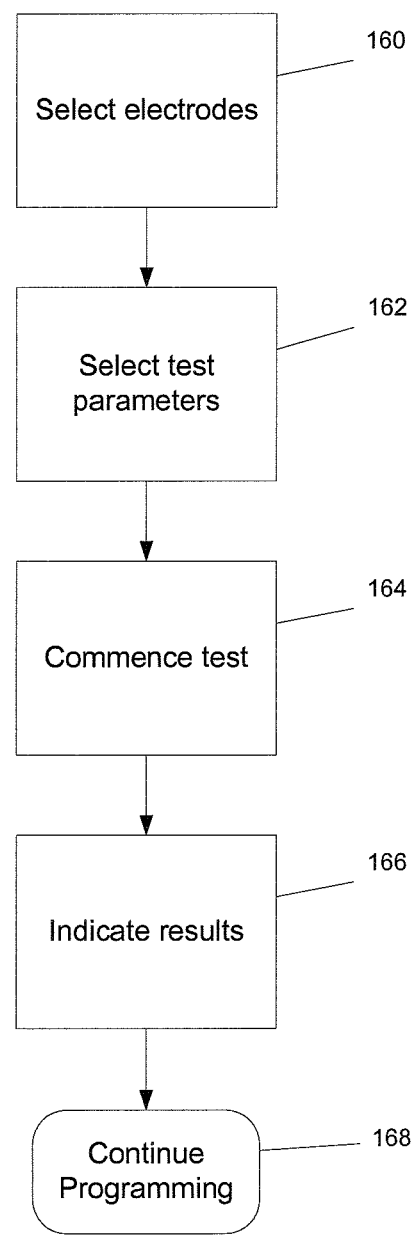
FIG. 8 is a flow chart for conducting an electrode impedance test for an implantable medical device.

FIG. 8 is a flow chart for pre-configuring an electrode impedance test. A user may select (160) electrodes 38 to be tested using electrode impedance panel 140 on controller 32. The user may then select (162) the test parameters at which the impedance test is conducted, again using electrode impedance panel 140 on controller 32. Once electrodes 38 and the test parameters have been selected, the user may commence (164) the electrode impedance test by selecting the Take Measurements button 48 on electrode impedance panel 140. Once the electrode impedance test has been conducted, results may be indicated (166) in results window 50 of electrode impedance panel 140, on out-of-range results panel 60, or all results panel 80 of controller 32. The user may then continue programming (168) implantable medical device 20.

In an embodiment, groups of electrodes 38 are selected based upon a task or range of tasks which may be performed. For example, it may be desirable to conduct tests on a select group of electrodes during a regular follow up visit to the medical professional. It may be appropriate to measure a subset of the entire number of plurality of electrodes during such a visit and routine test. However, during a testing procedure to trouble shoot lead or electrodes problems or issues it may be desirable to conduct tests on a greater number of electrodes than would be selected during a routine follow up test in order to gather more information about lead or electrode problems or issues encountered, or to even select all of the electrodes to be testing in such circumstance. Likewise, it may be desirable to group a plurality of electrodes to be tested during a procedure having minimal patient impact.

For instance, electrodes that are known to have uncomfortable or unpleasant side effects might be excluded from measurement or might be excluded from electrodes presented to a user for possible measurement. In an embodiment, a threshold for any such side effect may be established and electrodes that meet and/or exceed such threshold might be excluded from measurement or from presentation to a user for possible measurement. Similarly, electrodes know or thought to have little or no therapeutic benefit might be excluded from measurement or excluded from presentation for possible measurement. Combinations are also possible, for example, electrodes with some combination of little therapeutic benefit but some side effect might be excluded from measurement or presentation for measurement while an electrode or electrode combination with little therapeutic benefit but no side effect might be included in measurement or presentation for measurement or an electrode with some side effect but substantial therapeutic benefit might be included in measurement or presentation for measurement. A therapeutic benefit to side effect ratio might be established to help make such a determination.

In this case, a smaller number of electrodes may be selected in order to minimize the time and other impact on the patient. Thus, a plurality of different groups of electrodes may be pre-selected to fall into different categories of tests as may be beneficial. A user may then select a predetermined group of electrodes that may best fit the test being conducted. This may save the user from selecting from the entire list, or long list, of electrodes each time a test is to be conducted. A user may select, for example, the group associated with a routine follow up test and have the electrodes selected for test to be pre-populated in accordance with the predetermined group. In an embodiment, the user could still modify the electrodes to be tested from the starting point of the selected group.

In an embodiment, after an electrode, electrodes or a group of electrodes that have been selected, for example by modifying the electrode selection, then such modification could be used, at least in part, to determine which electrode, electrodes or groups of electrodes are measured or presented to a user for measurement in the future. For example, only electrodes that were selected by the user for measurement in the previous test would be presented to the user for a current test. The user may be presented with a list of electrodes selected or used during the previous visit or during a visit at a previous visit or a visit at a particular date and/or time. Alternatively, usage of an electrode, electrodes or groups of electrodes could be tracked and either the usage history of an electrode, electrodes or groups of electrodes could be presented to the user or the electrode, electrodes or groups of electrodes presented to the user for measurement could be based, at least in part, on such usage history such as by presenting the electrode, electrodes or groups of electrodes most commonly used, most recently used, least commonly used, etc.

In an embodiment, a group of electrodes to be tested could be selected or predetermined based upon the modality of the test procedure. As an example, a group could be predetermined that would conduct impedance measurements on selected electrodes that are current based. Another group could be predetermined that would conduct impedance measurements on selected electrodes that are voltage based. Other modalities of testing that are envisioned include, but are not limited to, real impedance, e.g., direct current measurement; complex impedance, e.g., alternating current measurement including capacitance and inductance measures; number of measurement or testing pulses; the timing measurement pulses or the time between measurement pulses; the manipulation of the data obtained from measurement, e.g., averaging of measurement sampling; and oversampling of measurement data. It is envisioned that various groups based upon measurement modality could be configured based upon, for example, which measurement technique would be fastest and which measurement technique would be most accurate or most comprehensive. It is to be recognized and understood that such groups are only exemplary and many other groups based upon measurement modality are envisioned.

Thus, embodiments of the controller for pre-configuring a test for implantable medical device electrodes, system and method therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A controller for an implantable medical device having a plurality of electrodes, said implantable medical device being capable of delivering therapeutic stimulation to a patient via said plurality of electrodes, comprising:
    a control module operatively coupled to said plurality of electrodes; and
    a user interface operatively coupled to said control module, said user interface providing at least partial control of said control module by a user;
    said control module being configured to:
        establish a plurality of predetermined groups of electrodes, at least one of said plurality of predetermined groups comprising a subset of said plurality of electrodes; and
        select at least one of said plurality of predetermined groups of electrodes via said user interface to establish at least one selected predetermined group of electrodes; and
        obtain a plurality of measurements of integrity metrics for electrodes, based upon whether said electrodes are contained within said at least one selected predetermined group of electrodes.

2. The controller as in claim 1 wherein said at least one of said plurality of predetermined groups are determined, at least in part, on a modality of measurement.

3. The controller as in claim 2 wherein said modality of measurement comprises at least one of current based impedance measurement, voltage based impedance measurement, real impedance, complex impedance, number of measurement pulses, timing of measurement pulses, sampling of measurement data and oversampling of measurement data.

4. The controller as in claim 1 wherein said control module is configured to obtain a plurality of measurements of integrity metrics of said electrodes included in said at least one selected predetermined group of electrodes selected via said user interface.

5. The controller as in claim 1 wherein said control module is configured to obtain a plurality of measurements of integrity metrics of said electrodes not included in said at least one selected predetermined group of electrodes selected via said user interface.

6. The controller as in claim 1 wherein said control module is configured to use a plurality of parameters selected via said user interface to obtain said plurality of measurements of integrity metrics.

7. The controller as in claim 6 wherein said plurality of parameters are selected from the group consisting of voltage, amplitude, pulse width, frequency, current, power and electrode polarity.

8. The controller as in claim 1 wherein said user interface is configured to present for possible measurement of an impedance value only ones of said plurality of electrodes having previously received a measurement of said impedance value comparative to a predetermined range.

9. The controller as in claim 1 wherein said user interface is configured to present for possible measurement of an impedance value only ones of said plurality of electrodes currently in use by said implantable medical device.

10. The controller as in claim 9 wherein said user interface is configured to present for possible measurement of said impedance value only ones of said plurality of electrodes having previously received a measurement of said impedance value comparative to a predetermined range.

11. The controller as in claim 9 wherein said user interface is configured to present for possible measurement of said impedance value only ones of said plurality of electrodes that have previously been selected by the user.

12. The controller as in claim 1 wherein said user interface is configured to present for possible measurement of an impedance value only ones of said plurality of electrodes that are associated as being at least one of free of side effects or free of side effects above a predetermined threshold.

13. A system for delivering therapeutic stimulation to a patient, comprising:
    an implantable medical device having a plurality of electrodes; and
    a controller, comprising:
        a control module operatively coupled to said plurality of electrodes;
        a user interface operatively coupled to said control module, said user interface providing control of said control module by a user; and
        said control module being configured to:
            establish a plurality of predetermined groups of electrodes, at least one of said plurality of predetermined groups comprising a subset of said plurality of electrodes; and
            select at least one of said plurality of predetermined groups of electrodes to establish at least one selected predetermined group of electrodes; and
            obtain a plurality of measurements of integrity metrics for electrodes based upon whether said electrodes are contained within said at least one selected predetermined group of electrodes.

14. The system as in claim 13 wherein said control module is configured to obtain a plurality of measurements of integrity metrics of said electrodes included in said at least one selected predetermined group of electrodes selected via said user interface.

15. The system as in claim 13 wherein said control module is configured to obtain a plurality of measurements of integrity metrics of said electrodes not included in said at least one selected predetermined group of electrodes selected via said user interface.

16. The system as in claim 13 wherein said control module is configured to use a plurality of parameters selected via said user interface to obtain said plurality of measurements of integrity metrics.

17. The system as in claim 16 wherein said plurality of parameters are selected from the group consisting of voltage, amplitude, pulse width, frequency, current, power and electrode polarity.

18. The system as in claim 13 wherein said user interface is configured to present for possible measurement of an impedance value only ones of said plurality of electrodes having previously received a measurement of said impedance value comparative to a predetermined range.

19. The system as in claim 13 wherein said user interface is configured to present for possible measurement of an impedance value only ones of said plurality of electrodes currently in use by said implantable medical device.

20. The system as in claim 19 wherein said user interface is configured to present for possible measurement of said impedance value only ones of said plurality of electrodes having previously received a measurement of said impedance value comparative to a predetermined range.

21. The system as in claim 20 wherein said user interface is configured to present for possible measurement of said impedance value only ones of said plurality of electrodes that have previously been selected by the user.

22. The system as in claim 13 wherein said user interface is configured to present for possible measurement of an impedance value only ones of said plurality of electrodes that are associated as being at least one of free of side effects or free of side effects above a predetermined threshold.

23. The system as in claim 13 wherein said at least one of said plurality of predetermined groups are determined, at least in part, on a modality of measurement.

24. The system as in claim 23 wherein said modality of measurement comprises at least one of current based impedance measurement, voltage based impedance measurement, real impedance, complex impedance, number of measurement pulses, timing of measurement pulses, sampling of measurement data and oversampling of measurement data.

25. A method for delivering therapeutic stimulation to a patient using an implantable medical device having a plurality of electrodes, comprising the steps of:

establishing a plurality of predetermined groups of said plurality of electrodes, at least one of said plurality of predetermined groups comprising a subset of said plurality of electrodes; and selecting at least one of said plurality of predetermined groups via a user interface to establish at least one selected predetermined group of electrodes;

obtaining a plurality of measurements of integrity metrics for electrodes based upon whether said electrodes are contained within said at least one selected predetermined group of electrodes.

26. The method as in claim 25 wherein said obtaining step utilizes said electrodes included in said at least one selected predetermined group of electrodes selected via said user interface.

27. The method as in claim 25 wherein said obtaining step utilizes said electrodes not included in said at least one selected predetermined group of electrodes selected via said user interface.

28. The method as in claim 25 wherein said obtaining step uses a plurality of parameters selected via said user interface.

29. The method as in claim 28 wherein said plurality of parameters are selected from the group consisting of voltage, amplitude, pulse width, frequency, current, power and electrode polarity.

30. The method as in claim 25 further comprising the step of presenting via said user interface for possible measurement of impedance value only ones of said plurality of electrodes having previously received a measurement of impedance value comparative to a predetermined range.

31. The method as in claim 30 wherein said presenting step presents for possible measurement of said impedance value only ones of said plurality of electrodes currently in use by said implantable medical device.

32. The method as in claim 31 wherein said presenting step presents for possible measurement of said impedance value only ones of said plurality of electrodes having previously received a measurement of said impedance value comparative to a predetermined range.

33. The method as in claim 31 wherein said presenting step presents for possible measurement of said impedance value only ones of said plurality of electrodes that have previously been selected by the user.

34. The method as in claim 30 wherein said presenting step presents for possible measurement of said impedance value only ones of said plurality of electrodes that are associated as being at least one of free of side effects or free of side effects above a predetermined threshold.

35. The method as in claim 25 wherein said plurality of predetermined groups in said establishing step is determined, at least in part, on a modality of measurement.

36. The method as in claim 35 wherein said modality of measurement comprises at least one of current based impedance measurement, voltage based impedance measurement, real impedance, complex impedance, number of measurement pulses, timing of measurement pulses, sampling of measurement data and oversampling of measurement data.

* * * * *

UNITED STATES PATENT AND TRADEMARK OFFICE
CERTIFICATE OF CORRECTION

PATENT NO. : 8,838,242 B2  
APPLICATION NO. : 12/112523  
DATED : September 16, 2014  
INVENTOR(S) : Goetz et al.

Page 1 of 1

It is certified that error appears in the above-identified patent and that said Letters Patent is hereby corrected as shown below:

IN THE CLAIMS:

Col. 12, Line 27: "of impedance value only ones" should read --of an impedance value only ones--

Col. 12, Line 28: "received a measurement of impedance" should read --received a measurement of said impedance--

Signed and Sealed this  
Fifth Day of May, 2015

Michelle K. Lee  
*Director of the United States Patent and Trademark Office*